United States Patent
Defossa et al.

(10) Patent No.: US 7,569,700 B2
(45) Date of Patent: Aug. 4, 2009

(54) SUBSTITUTED, BICYCLIC 8-PYRROLIDINOBENZIMIDAZOLES, METHODS FOR THEIR PRODUCTION AND THEIR USE AS MEDICAMENTS

(75) Inventors: Elisabeth Defossa, Idstein (DE); Karl Schoenafinger, Alzenau (DE); Gerhard Jaehne, Frankfurt (DE); Christian Buning, Bonn (DE); Georg Tschank, Essenheim (DE); Ulrich Werner, Miehlen (DE)

(73) Assignee: sanofi - aventis, Paris (FR)

( * ) Notice: Subject to any disclaimer, the term of this patent is extended or adjusted under 35 U.S.C. 154(b) by 0 days.

(21) Appl. No.: 11/855,224

(22) Filed: Sep. 14, 2007

(65) Prior Publication Data
US 2008/0090890 A1    Apr. 17, 2008

Related U.S. Application Data

(63) Continuation of application No. PCT/EP2006/002055, filed on Mar. 7, 2006.

(30) Foreign Application Priority Data
Mar. 19, 2005    (DE) .................. 10 2005 012 872

(51) Int. Cl.
*A61K 31/4184*    (2006.01)
*C07D 403/04*    (2006.01)

(52) U.S. Cl. ................... 548/305.1; 514/394
(58) Field of Classification Search ............. 548/305.1
See application file for complete search history.

(56) References Cited

U.S. PATENT DOCUMENTS

2002/0107396 A1    8/2002    Corbett et al.
2003/0008861 A1    1/2003    Lin et al.

*Primary Examiner*—Laura L. Stockton
(74) *Attorney, Agent, or Firm*—Brian R. Morrill

(57) ABSTRACT

The present invention relates to carboxamide derivative compounds of formula I

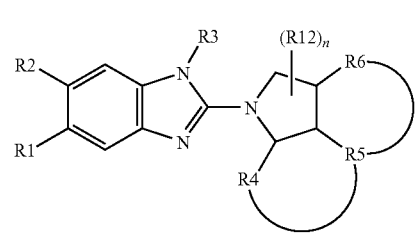

in which R1-R6 and R12 are hereinafter defined and together comprise carboximide derivatives for the therapeutic treatment of diabetes, hyperglycemia, lipid and carbohydrate metabolism disorders, arteriosclerotic manifestations and disorders and other blood sugar related disorders through a metabolic blood sugar-lowering action.

16 Claims, No Drawings

SUBSTITUTED, BICYCLIC 8-PYRROLIDINOBENZIMIDAZOLES, METHODS FOR THEIR PRODUCTION AND THEIR USE AS MEDICAMENTS

CROSS-REFERENCE TO RELATED APPLICATIONS

This application is a continuation of International Patent Application No. PCT/EP2006/002055 filed on Mar. 7, 2006 which is incorporated herein by reference in its entirety which also claims the benefit of priority of German Patent Appln. No. 10/2005012872.6 filed on Mar. 19, 2005.

FIELD OF THE INVENTION

The present invention relates generally to pharmaceutical compounds and compositions comprising them for the treatment of metabolic blood serum disorders and the physiological manifestations thereof. More specifically, the present invention relates to pharmaceutical compounds and compositions comprising them for the treatment of metabolic blood glucose disorders such as diabetes, hypoglycemia, hyperglycemia, hyperlipidemia, hypercholesterolemia and the like. More specifically, the present invention relates to substituted bicyclic 8-pyrrolidinobenzimidazoles and derivatives thereof for the treatment of metabolic blood disease.

BACKGROUND OF THE INVENTION

The compounds of the present invention are useful in the treatment and therapy of metabolic disorders of the blood, especially lipid and sugar metabolic disorders, through their ability to lower the triglyceride level and are therefore suitable for the prevention and treatment of type II diabetes and arteriosclerosis and the diverse diseased manifestations thereof.

Diabetes is a disease in which the body does not produce or properly use insulin.

Insulin is a hormone that is needed to convert sugar, starches and other food into energy needed for daily life. The cause of diabetes continues to be a mystery, although both genetics and environmental factors such as obesity and lack of exercise appear to play roles.

There are 20.8 million children and adults in the United States, or 7% of the population, who have diabetes. While an estimated 14.6 million have been diagnosed with diabetes, unfortunately, 6.2 million people (or nearly one-third) are unaware that they have the disease. Type 2 diabetes is the most common form of diabetes. In type 2 diabetes, either the body does not produce enough insulin or the cells ignore the insulin. Insulin is necessary for the body to be able to use sugar. Sugar is the basic fuel for the cells in the body, and insulin takes the sugar from the blood into the cells. When glucose builds up in the blood instead of going into cells, it can cause two problems:

Bodily tissues and the cells comprising them may be starved for energy.
Over time, high blood glucose levels may damage the eyes, kidneys, nerves or heart.

Conditions associated with diabetes include hyperglycemia and hypoglycemia which will increase ones risk for many serious complications including heart disease (cardiovascular disease), blindness (retinopathy), nerve damage (neuropathy), and kidney damage (nephropathy). The present invention relates to substituted bicyclic 8-pyrrolidinobenzimidazoles and to the physiologically compatible salts and physiologically functional derivatives thereof.

United States Published Patent Appln. No. 2006/0148855 to MacDonald et. al. describes structurally similar carboxamide derivative compounds processes for preparing such compounds, pharmaceutical compositions comprising them and their use in the treatment of chronic and acute pain, itching and urinary incontinence.

A wide variety of carboxamide derivative compounds of different structures are known in the art, for example those disclosed in U.S. Pat. No. 5,461,075 to O'Neill et. al. and European Patent No. 0 401 903 to Martodam et. al., UK Patent Application Number GB 222631315 and International Patent Application, Publication Numbers WO 92/09285 to Brand, L., U.S. Pat. No. 7,084,176 to Morie et. al. and U.S Published Appln. No. 2004/138454. Particularly notable examples of carboxamide derivative compounds or Vanilloid receptor modulators are capsaicin or trans 8-methyl-N-vanillyl-6-nonenamide which is isolated from the pepper plant, capsazepine (*Tetrahedron*, 53, 1997, 4791) and olvanil or N-(4-hydroxy-3-20 methoxybenzyl)oleamide (*J. Med. Chem.*, 36, 1993, 2595).

U.S. Pat. No. 6,723,730 to Bakthavatchalam et. al. discloses diaryl piperazine derivatives which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

U.S. Published Appln. No. 2006/142333 to Rami et.al. discloses carboxamide derivatives as Vanilloid receptor modulators and their use for the treatment of chronic and acute pain conditions.

However, it is an object of the present invention to provide compounds and compositions comprising them for the therapeutic treatment of diabetes, hyperglycemia and other blood sugar related disorders through a metabolic blood sugar-lowering action.

SUMMARY OF THE INVENTION

The present invention relates to carboxamide derivative compounds of formula I

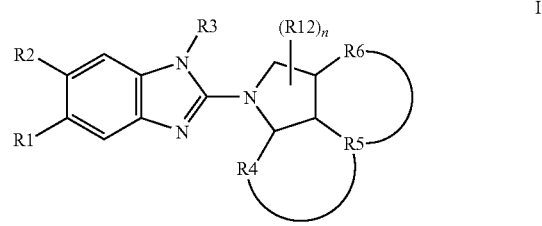

in which R1-R6 and R12 are hereinafter defined and together comprise carboximide derivatives for the therapeutic treatment of diabetes, hyperglycemia and other blood sugar related disorders through a metabolic blood sugar-lowering action.

DETAILED DESCRIPTION OF THE INVENTION

The present invention relates to carboxamide derivative compounds of the formula I, below:

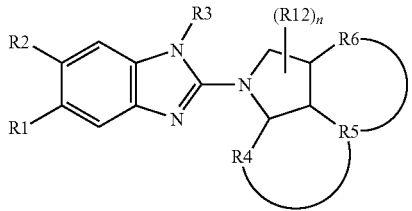

Formula I wherein,

R1 and R2 are each independently selected from the group consisting of H, CON(R20)R21, N(R22)COR23 or N(R24)R25, wherein R1 and R2 cannot both be hydrogen;

R20 and R21 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl or $(C_1-C_6)$-alkylene-$(C_6-C_{10})$-heterocycle, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl and $S(O)_2$—$(C_1-C_6)$-alkyl with the exception that R20 and R21 cannot be phenyl groups fused to nitrogen-containing 5-membered heteroaromatic rings;

R22 and R23 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or $S(O)_2$-aryl, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl and $S(O)_2$—$(C_1-C_6)$-alkyl;

R24 and R25 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or $S(O)_2$-aryl, where the alkyl, cycloalkyl, alkenyl, alkynyl, alkylene, aryl and heterocycle substituents may be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl and $S(O)_2$—$(C_1-C_6)$-alkyl;

R3 is selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl or heterocycle, where the alkyl, cycloalkyl, alkenyl, alkynyl, aryl and heterocycle substituents may be mono- or polysubstituted by F, Cl, Br, I, CN, $NO_2$, SH, OH, $(C_1-C_6)$-alkyl, —$CF_3$, —$OCF_3$, —$SCF_3$, $(C_2-C_6)$-alkenyl, $(C_2-C_6)$-alkynyl, OR7, OP(O)(OR7)$_2$, NR7R8, NR7CO(NR7)R8, COR7, OCOR7, OCOOR7, COOR7, CON(R7)R8, OCON(R7)R8, $(C_1-C_6)$-alkylene-OR7, $(C_1-C_6)$-alkylene-N(R7)R8, $(C_1-C_6)$-alkylene-NR7S(O)$_2$R7, $(C_1-C_6)$-alkylene-SR7, $(C_1-C_6)$-alkylene-S(O)R7, $(C_1-C_6)$-alkylene-S(O)$_2$R7, $(C_1-C_6)$-alkylene-S(O)$_2$N(R7)R8, $(C_1-C_6)$-alkylene-COR7, $(C_1-C_6)$-alkylene-COOR7, $(C_1-C_6)$-alkylene-CON(R7)R8, S(R7), S(O)R7, S(O)$_2$R7, $S(O)_2$N(R7)R8, NR7S(O)$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and heterocycle with the exception that R3 cannot be an un-substituted or substituted piperidin-4-yl R7 and R8 are each independently selected from the group consisting of H, $(C_1-C_6)$-alkyl, —$CF_3$, $(C_3-C_{10})$-cycloalkyl, $(C_6-C_{10})$-aryl, heterocycle, $(C_1-C_6)$-alkylene-CON(R9)R10, CON(R9)R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, S(O)R9, S(O)$_2$R9, $(C_1-C_4)$-alkylene-$(C_6-C_{10})$-aryl and $(C_1-C_4)$-alkylene-heterocycle;

R9 and R10 are each independently selected from the group consisting of H, $(C_1-C_6)$-alkyl, $(C_1-C_6)$-alkylene-$(C_6-C_{10})$-aryl, —$(C_6-C_{10})$-aryl, heterocycle and $(C_1-C_6)$-alkylene-heterocycle;

R4 and R5 together form a 3-5-membered alkylene chain in which one $CH_2$ group has been replaced by NR11 wherein R6 is H or R12, or R5 and R6 together form a 3- to 5-membered alkylene chain in which one $CH_2$ group has been replaced by NR11 wherein R4 is H or R12; wherein the 3- to 5-membered alkylene chain may in each case may be mono- or polysubstituted by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl)$_2$ or O—$(C_1-C_6)$-alkyl, where the alkyl groups may be mono- or polysubstituted by F, Cl, Br or I;

R11 is selected from the group consisting of H, $(C_1-C_6)$-alkyl, $(C_3-C_8)$-cycloalkyl, $(C_1-C_4)$-alkylene-aryl and $(C_1-C_4)$-alkylene-heterocycle;

R12 is selected from the group consisting of F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl)$_2$ and O—$(C_1-C_6)$-alkyl, where the alkyl groups may be mono- or polysubstituted by F, Cl, Br or I;

n is 0, 1 or 2;

excluding those compounds in which R1 or R2 are both simultaneously CON(R20)R21 and R3 is hydrogen or $CH_3$ and the pharmaceutically acceptable salts thereof.

Preferably, the present invention comprises compounds of formula I in which one or more of the substituents are each defined as follows:

R1 and R2 are each independently selected from the group consisting of H, CON(R20)R21, N(R22)COR23 and NR24R25, wherein the two R1 and R2 substituents cannot both be hydrogen;

R20 and R21 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl or $(C_1-C_6)$-alkylene-$(C_6-C_{10})$-heterocycle, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl and $S(O)_2$—$(C_1-C_6)$-alkyl;

wherein R20 and R21 cannot be a phenyl fused to a nitrogen-containing 5-membered heteroaromatic rings;

R22 and R23 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or $S(O)_2$-aryl, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl and $S(O)_2$—$(C_1-C_6)$-alkyl;

R24 and R25 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or $S(O)_2$-aryl, where the alkyl, cycloalkyl, alkenyl, alkynyl, alkylene, aryl and heterocycle substituents may be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, $S(O)$—$(C_1-C_6)$-alkyl and $S(O)_2$—$(C_1-C_6)$-alkyl;

R3 is selected from the group consisting of $(C_2-C_{10})$-alkyl, $(C_3-C_{10})$-cycloalkyl, $(C_2-C_{10})$-alkenyl, $(C_2-C_{10})$-alkynyl, $(C_6-C_{10})$-aryl or heterocycle, where the alkyl, cycloalkyl, alkenyl, alkynyl, aryl and heterocycle substituents may be mono- or polysubstituted by F, Cl, Br, I, CN, $NO_2$, SH, OH, $(C_1-C_6)$-alkyl, —$CF_3$, —$OCF_3$, —$SCF_3$, $(C_2-C_6)$-alkenyl, $(C_2-C_6)$-alkynyl, OR7, $OP(O)(OR7)_2$, NR7R8, N(R7)CON(R7)R8, COR7, OCOR7, OCOOR7, COOR7, CON(R7)R8, OCON(R7)R8, $(C_1-C_6)$-alkylene-OR7, $(C_1-C_6)$-alkylene-NR7R8, $(C_1-C_6)$-alkylene-NR7S$(O)_2$R7, $(C_1-C_6)$-alkylene-SR7, $(C_1-C_6)$-alkylene-S(O)R7, $(C_1-C_6)$-alkylene-S$(O)_2$R7, $(C_1-C_6)$-alkylene-S$(O)_2$N(R7)R8, $(C_1-C_6)$-alkylene-COR7, $(C_1-C_6)$-alkylene-COOR7, $(C_1-C_6)$-alkylene-CON(R7)R8, SR7, S(O)R7, S$(O)_2$R7, S$(O)_2$N(R7)R8, NR7S$(O)_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and heterocycle;

except that R3 cannot be an unsubstituted or substituted piperidin-4-yl;

R7 and R8 are each independently selected from the group consisting of $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S$(O)_2$R9, S(O)R9, S$(O)_2$R9, $(C_1-C_4)$-alkylene-$(C_6-C_{10})$-aryl and $(C_1-C_4)$-alkylene-heterocycle;

R9 and R10 are each independently selected from the group consisting of H, $(C_1-C_6)$-alkyl, $(C_1-C_6)$-alkylene-$(C_6-C_{10})$-aryl, —$(C_6-C_{10})$-aryl, heterocycle or $(C_1-C_6)$-alkylene-heterocycle;

R4 and R5 together form a 3-5-membered alkylene chain in which one $CH_2$ group has been replaced by NR11 wherein R6 is H or R12, or R5 and R6 together form a 3- to 5-membered alkylene chain in which one $CH_2$ group has been replaced by NR11 where R4 is H or R12; where the 3- to 5-membered alkylene chain may in each case may be mono- or polysubstituted by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ and O—$(C_1-C_6)$-alkyl, where the alkyl groups may be mono- or polysubstituted by F, Cl, Br or I;

R11 is selected from the group consisting of H, $(C_1-C_6)$-alkyl, $(C_3-C_8)$-cycloalkyl, $(C_1-C_4)$-alkylene-aryl and $(C_1-C_4)$-alkylene-heterocycle;

R12 is selected from the group consisting of F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ and O—$(C_1-C_6)$-alkyl, where the alkyl groups may be mono- or polysubstituted by F, Cl, Br or I;

n is 0, 1 or 2;

and pharmaceutically acceptable salts thereof.

More preferably, the present invention comprises compounds of formula I in which one or more of the substituents are each defined as follows:

R1 and R2 are each independently selected from the group consisting of H, CON(R20)R21, N(R22)COR23 and N(R24)R25, where the two R1 and R2 substituents cannot both be hydrogen;

R20 and R21 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl and $(C_1-C_6)$-alkylene-$(C_6-C_{10})$-heterocycle, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, $S(O)$—$(C_1-C_6)$-alkyl or $S(O)_2$—$(C_1-C_6)$-alkyl;

wherein R20 and R21 cannot be a phenyl fused to a nitrogen-containing 5-membered heteroaromatic rings;

R22 and R23 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle and $S(O)_2$-aryl, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, $S(O)$—$(C_1-C_6)$-alkyl or $S(O)_2$—$(C_1-C_6)$-alkyl;

R24, R25 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or $S(O)_2$-aryl, where the alkyl, cycloalkyl, alkenyl, alkynyl, alkylene, aryl and heterocycle substituents may be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, $S(O)$—$(C_1-C_6)$-alkyl or $S(O)_2$—$(C_1-C_6)$-alkyl;

R3 is selected from the group consisting of $(C_2-C_{10})$-alkyl, $(C_3-C_{10})$-cycloalkyl, $(C_2-C_{10})$-alkenyl, $(C_2-C_{10})$-alkynyl, $(C_6-C_{10})$-aryl or heterocycle, where the alkyl, cycloalkyl, alkenyl, alkynyl, aryl and heterocycle substituents may be mono- or polysubstituted by F, Cl, Br, I, CN, $NO_2$, SH, OH, $(C_1-C_6)$-alkyl, —$CF_3$, —$OCF_3$, —$SCF_3$, $(C_2-C_6)$-alkenyl, $(C_2-C_6)$-alkynyl, OR7, $OP(O)(OR7)_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7S$(O)_2$R7, $(C_1-C_6)$-alkylene-SR7, $(C_1-C_6)$-alkylene-S(O)R7, $(C_1-C_6)$-alkylene-S$(O)_2$R7, $(C_1-C_6)$-alkylene-S$(O)_2$NR7R8, $(C_1-C_6)$-alkylene-COR7, $(C_1-C_6)$-alkylene-COOR7, $(C_1-C_6)$-alkylene-CONR7R8, SR7, S(O)R7, S$(O)_2$R7, S$(O)_2$NR7R8, NR7S$(O)_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl or heterocycle;

except that R3 cannot be an unsubstituted or substituted piperidin-4-yl;

R7 and R8 are each independently selected from the group consisting of H, $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S$(O)_2$ R9, S(O)R9, S(O)$_2$R9, (C$_1$-C$_4$)-alkylene-(C$_6$-C$_{10}$)-aryl and (C$_1$-C$_4$)-alkylene-heterocycle;

R9 and R10 are each independently selected from the group consisting of H, (C$_1$-C$_6$)-alkyl, (C$_1$-C$_6$)-alkylene-(C$_6$-C$_{10}$)-aryl, —(C$_6$-C$_{10}$)-aryl, heterocycle and (C$_1$-C$_6$)-alkylene-heterocycle;

R4 and R5 together form a 3-5-membered alkylene chain in which one CH$_2$ group has been replaced by NR11 when R6 is H or R12, or R5 and R6 together form a 3- to 5-membered alkylene chain in which one CH$_2$ group has been replaced by NR11 when R4 is H or R12; where the 3- to 5-membered alkylene chain may in each case may be mono- or polysubstituted by F, Cl, Br, I, (C$_1$-C$_6$)-alkyl, (C$_3$-C$_8$)-cycloalkyl, NH$_2$, NH(C$_1$-C$_6$)-alkyl, NH(C$_3$-C$_7$)-cycloalkyl, N((C$_1$-C$_6$)-alkyl)$_2$ or O—(C$_1$-C$_6$)-alkyl, where the alkyl groups may be mono- or polysubstituted by F, Cl, Br or I;

R11 is selected from the group consisting of H, (C$_1$-C$_6$)-alkyl, (C$_3$-C$_8$)-cycloalkyl, (C$_1$-C$_4$)-alkylene-aryl and (C$_1$-C$_4$)-alkylene-heterocycle;

R12 is selected from the group consisting of F, Cl, Br, I, (C$_1$-C$_6$)-alkyl, (C$_3$-C$_8$)-cycloalkyl, NH$_2$, NH(C$_1$-C$_6$)-alkyl, NH(C$_3$-C$_7$)-cycloalkyl, N((C$_1$-C$_6$)-alkyl)$_2$ and O—(C$_1$-C$_6$)-alkyl, where the alkyl groups may be mono- or polysubstituted by F, Cl, Br or I;

n is 0, 1 or 2;

and the pharmaceutically acceptable salts thereof.

Particularly preferable compounds of the present invention are those of formula I in which one or more of the substituents are defined as follows:

R1 and R2 are each independently selected from the group consisting of H, benzylaminocarbonyl, benzoylamino, where the benzylaminocarbonyl and benzoylamino substituents may be mono- or polysubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$;

wherein both R1 and R2 moieties cannot be hydrogen;

R3 is selected from the group consisting of (C$_2$-C$_{10}$)-alkenyl and benzyl, wherein the benzyl radical may be mono- or polysubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$;

R4 and R5 together form a 3-5-membered alkylene chain in which one CH$_2$ group has been replaced by NH, where the alkyl groups may be mono- or poly-substituted by F, Cl, Br or I;

R11 is selected from the group consisting of H, (C$_1$-C$_6$)-alkyl, (C$_3$-C$_8$)-cycloalkyl, (C$_1$-C$_4$)-alkylene-aryl and (C$_1$-C$_4$)-alkylene-heterocycle;

n is 0;

and the pharmaceutically acceptable salts thereof.

The invention further relates to the use of the compounds of formula I

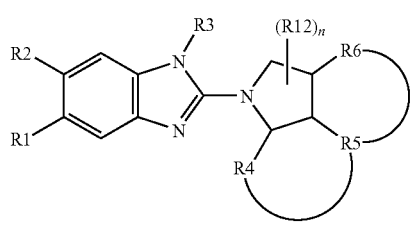

I wherein:

R1 and R2 are each independently selected from the group consisting of H, CON(R20)R21, N(R22)COR23 and NR24R25;

R20 and R21 are each independently selected from the group consisting of H, (C$_1$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl, heterocycle, (C$_1$-C$_6$)-alkylene-(C$_6$-C$_{10}$)-aryl and (C$_1$-C$_6$)-alkylene-(C$_6$-C$_{10}$)-heterocycle, where the alkyl, cycloalkyl, alkenyl, alkynyl, alkylene, aryl and heterocycle substituents may each be mono- or polysubstituted by F, Cl, Br, I, CN, NO$_2$, SH, OH, (C$_1$-C$_6$)-alkyl, O—(C$_1$-C$_6$)-alkyl, S—(C$_1$-C$_6$)-alkyl, S(O)—(C$_1$-C$_6$)-alkyl or S(O)$_2$—(C$_1$-C$_6$)-alkyl;

R22 and R23 are each independently selected from the group consisting of H, (C$_1$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl, heterocycle, (C$_1$-C$_6$)-alkylene-(C$_6$-C$_{10}$)-aryl, (C$_1$-C$_6$)-alkylene-(C$_6$-C$_{10}$)-heterocycle and S(O)$_2$-aryl, where the alkyl, cycloalkyl, alkenyl, alkynyl, alkylene, aryl and heterocycle substituents may each be mono- or poly-substituted by F, Cl, Br, I, CN, NO$_2$, SH, OH, (C$_1$-C$_6$)-alkyl, O—(C$_1$-C$_6$)-alkyl, S—(C$_1$-C$_6$)-alkyl, S(O)—(C$_1$-C$_6$)-alkyl or S(O)$_2$—(C$_1$-C$_6$)-alkyl;

R24 and R25 are each independently selected from the group consisting of H, (C$_1$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl, heterocycle, (C$_1$-C$_6$)-alkylene-(C$_6$-C$_{10}$)-aryl, (C$_1$-C$_6$)-alkylene-(C$_6$-C$_{10}$)-heterocycle and S(O)$_2$-aryl, where the alkyl, cycloalkyl, alkenyl, alkynyl, alkylene, aryl and heterocycle substituents may be mono- or polysubstituted by F, Cl, Br, I, CN, NO$_2$, SH, OH, (C$_1$-C$_6$)-alkyl, O—(C$_1$-C$_6$)-alkyl, S—(C$_1$-C$_6$)-alkyl, S(O)—(C$_1$-C$_6$)-alkyl or S(O)$_2$—(C$_1$-C$_6$)-alkyl;

R3 is selected from the group consisting of H, (C$_1$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl and heterocycle, where the alkyl, cycloalkyl, alkenyl, alkynyl, aryl and heterocycle substituents may be mono- or polysubstituted by F, Cl, Br, I, CN, NO$_2$, SH, OH, (C$_1$-C$_6$)-alkyl, —CF$_3$, —OCF$_3$, —SCF$_3$, (C$_2$-C$_6$)-alkenyl, (C$_2$-C$_6$)-alkynyl, OR7, OP(O)(OR7)$_2$, N(R7)R8, N(R7)CON(R7)R8, COR7, OCOR7, OCOOR7, COOR7, CON(R7)R8, OCON(R7)R8, (C$_1$-C$_6$)-alkylene-OR7, (C$_1$-C$_6$)-alkylene-NR7R8, (C$_1$-C$_6$)-alkylene-NR7S(O)$_2$R7, (C$_1$-C$_6$)-alkylene-SR7, (C$_1$-C$_6$)-alkylene-S(O)R7, (C$_1$-C$_6$)-alkylene-S(O)$_2$R7, (C$_1$-C$_6$)-alkylene-S(O)$_2$NR7R8, (C$_1$-C$_6$)-alkylene-COR7, (C$_1$-C$_6$)-alkylene-COOR7, (C$_1$-C$_6$)-alkylene-CONR7R8, SR7, S(O)R7, S(O)$_2$R7, S(O)$_2$NR7R8, NR7S(O)$_2$R7, (C$_1$-C$_6$)-alkylene-(C$_3$-C$_{10}$)-cycloalkyl, (C$_1$-C$_6$)-alkylene-(C$_6$-C$_{10}$)-aryl, (C$_1$-C$_6$)-alkylene-heterocycle, (C$_3$-C$_{10}$)-cycloalkyl, (C$_6$-C$_{10}$)-aryl or heterocycle;

R7 and R8 are each independently selected from the group consisting of H, (C$_1$-C$_6$)-alkyl, —CF$_3$, (C$_3$-C$_{10}$)-cycloalkyl, (C$_6$-C$_{10}$)-aryl, heterocycle, (C$_1$-C$_6$)-alkylene-CON(R9)R10, CON(R9)R10, (C$_1$-C$_6$)-alkylene-COOR9, COOR9, COR9, (C$_1$-C$_6$)-alkylene-CO(R9), (C$_1$-C$_6$)-alkylene-OR9, (C$_1$-C$_6$)-alkylene-NR9R10, (C$_1$-C$_6$)-alkylene-SR9, (C$_1$-C$_6$)-alkylene-S(O)R9, (C$_1$-C$_6$)-alkylene-S(O)$_2$R9, S(O)R9, S(O)$_2$R9, (C$_1$-C$_4$)-alkylene-(C$_6$-C$_{10}$)-aryl and (C$_1$-C$_4$)-alkylene-heterocycle;

R9 and R10 are each independently selected from the group consisting of H, (C$_1$-C$_6$)-alkyl, (C$_1$-C$_6$)-alkylene-(C$_6$-C$_{10}$)-aryl, (C$_6$-C$_{10}$)-aryl, heterocycle and (C$_1$-C$_6$)-alkylene-heterocycle;

R4 and R5 together form a 3-5-membered alkylene chain in which one $CH_2$ group has been replaced by NR11 where R6 is H or R12, or R5 and R6 together form a 3- to 5-membered alkylene chain in which one $CH_2$ group has been replaced by NR11 where R4 is H or R12; where the 3- to 5-membered alkylene chain may in each case may be mono- or polysubstituted by F, Cl, Br, I, $(C_1$-$C_6)$-alkyl, $(C_3$-$C_8)$-cycloalkyl, $NH_2$, $NH(C_1$-$C_6)$-alkyl, $NH(C_3$-$C_7)$-cycloalkyl, $N((C_1$-$C_6)$-alkyl$)_2$ or O—$(C_1$-$C_6)$-alkyl, where the alkyl groups may be mono- or polysubstituted by F, Cl, Br or I;

R11 is selected from the group consisting of H, $(C_1$-$C_6)$-alkyl, $(C_3$-$C_8)$-cycloalkyl, $(C_1$-$C_4)$-alkylene-aryl and $(C_1$-$C_4)$-alkylene-heterocycle;

R12 is selected from the group consisting of F, Cl, Br, I, $(C_1$-$C_6)$-alkyl, $(C_3$-$C_8)$-cycloalkyl, $NH_2$, $NH(C_1$-$C_6)$-alkyl, $NH(C_3$-$C_7)$-cycloalkyl, $N((C_1$-$C_6)$-alkyl$)_2$ and O—$(C_1$-$C_6)$-alkyl, where the alkyl groups may be mono- or polysubstituted by F, Cl, Br or I;

n is 0, 1 or 2;

and the pharmaceutically acceptable salts thereof for producing a drug for lowering blood sugar.

The invention relates to compounds of the formula I, in the form of their racemates, racemic mixtures and pure enantiomers, and also to their diastereomers and mixtures thereof.

When substituents or substituents can occur more than once in the compounds of the formula I, they may all each independently have the definitions specified and be the same or different.

Owing to their higher water solubility, pharmaceutically acceptable salts are particularly suitable for medical applications compared to the starting or base compounds. These salts must have a pharmaceutically acceptable anion or cation. Suitable pharmaceutically acceptable acid addition salts of the inventive compounds are salts of inorganic acids such as hydrochloric acid, hydrobromic acid, phosphoric acid, metaphosphoric acid, nitric acid and sulfuric acid, and organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion, for example trifluoroacetate, are likewise included in the scope of the invention as useful intermediates for the preparation or purification of pharmaceutically acceptable salts and/or for the use in non-therapeutic, for example in vitro, applications.

The term "physiologically functional derivative" used here refers to any physiologically compatible derivative of an inventive compound of the formula I, for example an ester which, on administration to a mammal, for example the human, is capable (directly or indirectly) of forming a compound of the formula I or an active metabolite thereof.

The physiologically functional derivatives also include prodrugs of the inventive compounds. Such prodrugs can be metabolized in vivo to give an inventive compound. These prodrugs may or may not themselves be active.

The inventive compounds may also be present in various polymorphic forms, for example as amorphous and crystalline polymorphic forms. All polymorphic forms of the inventive compounds are included within the scope of the invention and are a further aspect of the invention.

Hereinafter, all references to "compound(s) of the formula (I)" relate to compound(s) of the formula I as described above, and also their salts, solvates and physiologically functional derivatives as described herein.

An alkyl radical is understood to mean a straight-chain or branched hydrocarbon chain having one or more carbons, for example methyl, ethyl, isopropyl, tert-butyl, hexyl.

The alkyl substituents may be mono- or polysubstituted by suitable groups, for example:

F, Cl, Br, I, $CF_3$, $NO_2$, $N_3$, CN, COOH, COO$(C_1$-$C_6)$alkyl, $CONH_2$, $CONH(C_1$-$C_6)$alkyl, $CON[(C_1$-$C_6)$alkyl$]_2$, cycloalkyl, $(C_2$-$C_6)$-alkenyl, $(C_2$-$C_6)$-alkynyl, O—$(C_1$-$C_6)$-alkyl, O—CO—$(C_1$-$C_6)$-alkyl, O—CO—$(C_1$-$C_6)$-aryl, O—CO—$(C_1$-$C_6)$-heterocycle;

$PO_3H_2$, $SO_3H$, $SO_2$—$NH_2$, $SO_2NH(C_1$-$C_6)$-alkyl, $SO_2N[(C_1$-$C_6)$-alkyl$]_2$, S—$(C_1$-$C_6)$-alkyl, S—$(CH_2)_n$-aryl, S—$(CH_2)_n$-heterocycle, SO—$(C_1$-$C_6)$-alkyl, SO—$(CH_2)_n$-aryl, SO—$(CH_2)_n$-heterocycle, $SO_2$—$(C_1$-$C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N((C_1$-$C_6)$-alkyl$)(CH_2)_n$-aryl, $SO_2$—$N((C_1$-$C_6)$-alkyl$)(CH_2)_n$-heterocycle, $SO_2$—$N((CH_2)_n$-aryl$)_2$, $SO_2$—$N((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, O—$(C_1$-$C_6)$-alkyl, $(C_1$-$C_6)$-alkyl or $NH_2$;

C(=NH)(NH$_2$), $NH_2$, NH—$(C_1$-$C_6)$-alkyl, $N((C_1$-$C_6)$-alkyl$)_2$, $NH(C_1$-$C_7)$-acyl, NH—COO—$(C_1$-$C_6)$-alkyl, NH—CO-aryl, NH—CO-heterocycle, NH—COO-aryl, NH—COO-heterocycle, NH—CO—NH—$(C_1$-$C_6)$-alkyl, NH—CO—NH-aryl, NH—CO—NH-heterocycle, $N((C_1$-$C_6)$-alkyl$)$-CO—$(C_1$-$C_6)$-alkyl, $N((C_1$-$C_6)$-alkyl$)$-COO—$(C_1$-$C_6)$-alkyl, $N((C_1$-$C_6)$-alkyl$)$-CO-aryl, $N((C_1$-$C_6)$-alkyl$)$-CO-heterocycle, $N((C_1$-$C_6)$-alkyl$)$-COO-aryl, $N((C_1$-$C_6)$-alkyl$)$-COO-heterocycle, $N((C_1$-$C_6)$-alkyl$)$-CO—NH—$(C_1$-$C_6)$-alkyl), $N((C_1$-$C_6)$-alkyl$)$-CO—NH-aryl, $N((C_1$-$C_6)$-alkyl$)$-CO—NH-heterocycle, $N((C_1$-$C_6)$-alkyl$)$-CO—N$((C_1$-$C_6)$-alkyl$)_2$, $N((C_1$-$C_6)$-alkyl$)$-CO—N$((C_1$-$C_6)$-alkyl$)$-aryl, $N((C_1$-$C_6)$-alkyl$)$-CO—N$((C_1$-$C_6)$-alkyl$)$-heterocycle, $N((C_1$-$C_6)$-alkyl$)$-CO—N-(aryl)$_2$, $N((C_1$-$C_6)$-alkyl$)$-CO—N-(heterocycle)$_2$, N(aryl)-CO—$(C_1$-$C_6)$-alkyl, N(heterocycle)-CO—$(C_1$-$C_6)$-alkyl, N(aryl)-COO—$(C_1$-$C_6)$-alkyl, N(heterocycle)-COO—$(C_1$-$C_6)$-alkyl, N(aryl)-CO-aryl, N(heterocycle)-CO-aryl, N(aryl)-COO-aryl, N(heterocycle)-COO-aryl, N(aryl)-CO—NH—$(C_1$-$C_6)$-alkyl), N(heterocycle)-CO—NH—$(C_1$-$C_6)$-alkyl), N(aryl)-CO—NH-aryl, N(heterocycle)-CO—NH-aryl, N(aryl)-CO—N$((C_1$-$C_6)$-alkyl$)_2$, N(heterocycle)-CO—N$((C_1$-$C_6)$-alkyl$)_2$, N(aryl)-CO—N$((C_1$-$C_6)$-alkyl$)$-aryl, N(heterocycle)-CO—N$((C_1$-$C_6)$-alkyl$)$-aryl, N(aryl)-CO—N-(aryl)$_2$, N(heterocycle)-CO—N-(aryl)$_2$, aryl, O—$(CH_2)_n$-aryl and O—$(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl$)_2$, $SO_2$—$CH_3$, COOH, COO—$(C_1$-$C_6)$-alkyl or $CONH_2$.

An alkenyl radical is understood to mean a straight-chain or branched hydrocarbon chain having two or more carbons and one or more double bonds, for example vinyl, allyl, pentenyl, 2-methyl-but-2-en-4-yl.

The alkenyl substituents may be mono- or polysubstituted by suitable groups, for example:

F, Cl, Br, I, $CF_3$, $NO_2$, $N_3$, CN, COOH, COO$(C_1$-$C_6)$alkyl, $CONH_2$, $CONH(C_1$-$C_6)$alkyl, $CON[(C_1$-$C_6)$alkyl$]_2$, cycloalkyl, $(C_2-C_6)$-alkenyl, $(C_2-C_6)$-alkynyl, O—$(C_1$-$C_6)$-alkyl, O—CO—$(C_1-C_6)$-alkyl, O—CO—$(C_1-C_6)$-aryl, O—CO—$(C_1-C_6)$-heterocycle;

$PO_3H_2$, $SO_3H$, $SO_2$—$NH_2$, $SO_2NH(C_1-C_6)$-alkyl, $SO_2N$[$(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N((C_1-C_6)$-alkyl$)(CH_2)_n$-aryl, $SO_2$—$N((C_1-C_6)$-alkyl$)(CH_2)_n$-heterocycle, $SO_2$—$N((CH_2)_n$-aryl$)_2$, $SO_2$—$N((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, O—$(C_1-C_6)$-alkyl, $(C_1-C_6)$-alkyl or $NH_2$;

C(=NH)(NH$_2$), NH$_2$, NH—$(C_1-C_6)$-alkyl, N($(C_1-C_6)$-alkyl)$_2$, NH$(C_1-C_7)$-acyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, N($(C_1-C_6)$-alkyl)-CO—$(C_1-C_6)$-alkyl, N($(C_1-C_6)$-alkyl)-COO—$(C_1-C_6)$-alkyl, N($(C_1-C_6)$-alkyl)-CO-aryl, N($(C_1-C_6)$-alkyl)-CO-heterocycle, N($(C_1-C_6)$-alkyl)-COO-aryl, N($(C_1-C_6)$-alkyl)-COO-heterocycle, N($(C_1-C_6)$-alkyl)-CO—NH—$(C_1-C_6)$-alkyl), N($(C_1-C_6)$-alkyl)-CO—NH-aryl, N($(C_1-C_6)$-alkyl)-CO—NH-heterocycle, N($(C_1-C_6)$-alkyl)-CO—N($(C_1-C_6)$-alkyl)$_2$, N($(C_1-C_6)$-alkyl)-CO—N$((C_1-C_6)$-alkyl)-aryl, N($(C_1-C_6)$-alkyl)-CO—N$((C_1-C_6)$-alkyl)-heterocycle, N($(C_1-C_6)$-alkyl)-CO—N-(aryl)$_2$, N($(C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—N($(C_1-C_6)$-alkyl)$_2$, N(heterocycle)-CO—N($(C_1-C_6)$-alkyl)$_2$, N(aryl)-CO—N$((C_1-C_6)$-alkyl)-aryl, N(heterocycle)-CO—N$((C_1-C_6)$-alkyl)-aryl, N(aryl)-CO—N-(aryl)$_2$, N(heterocycle)-CO—N-(aryl)$_2$, aryl, O—$(CH_2)_n$-aryl and O—$(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N$((C_1-C_6)$-alkyl)$_2$, $SO_2$—$CH_3$, COOH, COO—$(C_1-C_6)$-alkyl or $CONH_2$.

An alkynyl radical is understood to mean a straight-chain or branched hydrocarbon chain having two or more carbons and one or more triple bonds, for example ethynyl, propynyl, butynyl, hexynyl.

The alkynyl substituents may be mono- or polysubstituted by suitable groups, for example:

F, Cl, Br, I, $CF_3$, $NO_2$, $N_3$, CN, COOH, COO$(C_1-C_6)$alkyl, $CONH_2$, $CONH(C_1-C_6)$alkyl, CON[$(C_1-C_6)$alkyl]$_2$, cycloalkyl, $(C_2-C_6)$-alkenyl, $(C_2-C_6)$-alkynyl, O—$(C_1-C_6)$-alkyl, O—CO—$(C_1-C_6)$-alkyl, O—CO—$(C_1-C_6)$-aryl, O—CO—$(C_1-C_6)$-heterocycle;

$PO_3H_2$, $SO_3H$, $SO_2$—$NH_2$, $SO_2NH(C_1-C_6)$-alkyl, $SO_2N$[$(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N((C_1-C_6)$-alkyl$)(CH_2)_n$-aryl, $SO_2$—$N((C_1-C_6)$-alkyl$)(CH_2)_n$-heterocycle, $SO_2$—$N((CH_2)_n$-aryl$)_2$, $SO_2$—$N((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, O—$(C_1-C_6)$-alkyl, $(C_1-C_6)$-alkyl or $NH_2$;

C(=NH)(NH$_2$), NH$_2$, NH—$(C_1-C_6)$-alkyl, N($(C_1-C_6)$-alkyl)$_2$, NH$(C_1-C_7)$-acyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, N($(C_1-C_6)$-alkyl)-CO—$(C_1-C_6)$-alkyl, N($(C_1-C_6)$-alkyl)-COO—$(C_1-C_6)$-alkyl, N($(C_1-C_6)$-alkyl)-CO-aryl, N($(C_1-C_6)$-alkyl)-CO-heterocycle, N($(C_1-C_6)$-alkyl)-COO-aryl, N($(C_1-C_6)$-alkyl)-COO-heterocycle, N($(C_1-C_6)$-alkyl)-CO—NH—$(C_1-C_6)$-alkyl), N($(C_1-C_6)$-alkyl)-CO—NH-aryl, N($(C_1-C_6)$-alkyl)-CO—NH-heterocycle, N($(C_1-C_6)$-alkyl)-CO—N($(C_1-C_6)$-alkyl)$_2$, N($(C_1-C_6)$-alkyl)-CO—N$((C_1-C_6)$-alkyl)-aryl, N($(C_1-C_6)$-alkyl)-CO—N$((C_1-C_6)$-alkyl)-heterocycle, N($(C_1-C_6)$-alkyl)-CO—N-(aryl)$_2$, N($(C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—N($(C_1-C_6)$-alkyl)$_2$, N(heterocycle)-CO—N($(C_1-C_6)$-alkyl)$_2$, N(aryl)-CO—N$((C_1-C_6)$-alkyl)-aryl, N(heterocycle)-CO—N$((C_1-C_6)$-alkyl)-aryl, N(aryl)-CO—N-(aryl)$_2$, N(heterocycle)-CO—N-(aryl)$_2$, aryl, O—$(CH_2)_n$-aryl and O—$(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N$((C_1-C_6)$-alkyl)$_2$, $SO_2$—$CH_3$, COOH, COO—$(C_1-C_6)$-alkyl or $CONH_2$.

An aryl radical is understood to mean a phenyl, naphthyl, biphenyl, tetrahydronaphthyl, alpha- or beta-tetralonyl, indanyl or indan-1-onyl radical.

The aryl substituents may be mono- or polysubstituted by suitable groups, for example:

F, Cl, Br, I, $CF_3$, $NO_2$, $N_3$, CN, COOH, COO$(C_1-C_6)$alkyl, $CONH_2$, $CONH(C_1-C_6)$alkyl, CON[$(C_1-C_6)$alkyl]$_2$, cycloalkyl, $(C_2-C_6)$-alkenyl, $(C_2-C_6)$-alkynyl, O—$(C_1-C_6)$-alkyl, O—CO—$(C_1-C_6)$-alkyl, O—CO—$(C_1-C_6)$-aryl, O—CO—$(C_1-C_6)$-heterocycle;

$PO_3H_2$, $SO_3H$, $SO_2$—$NH_2$, $SO_2NH(C_1-C_6)$-alkyl, $SO_2N$[$(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N((C_1-C_6)$-alkyl$)(CH_2)_n$-aryl, $SO_2$—$N((C_1-C_6)$-alkyl$)(CH_2)_n$-heterocycle, $SO_2$—$N((CH_2)_n$-aryl$)_2$, $SO_2$—$N((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, O—$(C_1-C_6)$-alkyl, $(C_1-C_6)$-alkyl or $NH_2$;

C(=NH)(NH$_2$), NH$_2$, NH—$(C_1-C_6)$-alkyl, N($(C_1-C_6)$-alkyl)$_2$, NH$(C_1-C_7)$-acyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, N($(C_1-C_6)$-alkyl)-CO—$(C_1-C_6)$-alkyl, N($(C_1-C_6)$-alkyl)-COO—$(C_1-C_6)$-alkyl, N($(C_1-C_6)$-alkyl)-CO-aryl, N($(C_1-C_6)$-alkyl)-CO-heterocycle, N($(C_1-C_6)$-alkyl)-COO-aryl, N($(C_1-C_6)$-alkyl)-COO-heterocycle, N($(C_1-C_6)$-alkyl)-CO—NH—$(C_1-C_6)$-alkyl), N($(C_1-C_6)$-alkyl)-CO—NH-aryl, N($(C_1-C_6)$-alkyl)-CO—NH-heterocycle, N($(C_1-C_6)$- alkyl)-CO—N(($C_1$-$C_6$)-alkyl)$_2$, N(($C_1$-$C_6$)-alkyl)-CO—N (($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N (($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl and O—($CH_2$)$_n$-heterocycle, where n may be 0-6, where the aryl radical or heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

A cycloalkyl radical is understood to mean a ring system which comprises one or more rings and is present in saturated or partially unsaturated form (with one or two double bonds), and is formed exclusively from carbon atoms, for example cyclopropyl, cyclopentyl, cyclopentenyl, cyclohexyl or adamantyl.

The cycloalkyl substituents may be mono- or polysubstituted by suitable groups, for example:

F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2$NH($C_1$-$C_6$)-alkyl, $SO_2$N [($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N(($C_1$-$C_6$)-alkyl)($CH_2$)$_n$-aryl, $SO_2$—N(($C_1$-$C_6$)-alkyl)($CH_2$)$_n$-heterocycle, $SO_2$—N(($CH_2$)$_n$-aryl)$_2$, $SO_2$—N(($CH_2$)$_n$-heterocycle)$_2$ where n may be 0-6 and the aryl radical or heterocyclic radical may be up to disubstituted by F, Cl, Br, OH, $CF_3$, $NO_2$, CN, $OCF_3$, O—($C_1$-$C_6$)-alkyl, ($C_1$-$C_6$)-alkyl or $NH_2$;

C(=NH)($NH_2$), $NH_2$, NH—($C_1$-$C_6$)-alkyl, N(($C_1$-$C_6$)-alkyl)$_2$, NH($C_1$-$C_7$)-acyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N(($C_1$-$C_6$)-alkyl)-CO—($C_1$-$C_6$)-alkyl, N(($C_1$-$C_6$)-alkyl)-COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N (($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N (($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl and O—($CH_2$)$_n$-heterocycle, where n may be 0-6, where the aryl radical or heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

Heterocycle, heterocycle and heterocyclic radical are understood to mean rings and ring systems which, apart from carbon, also contain heteroatoms, for example nitrogen, oxygen or sulfur. This definition also includes ring systems in which the heterocycle or the heterocyclic radical is fused to benzene rings. The heterocycle or the heterocyclic radical may be aromatic, saturated aliphatic or partially unsaturated aliphatic.

Suitable heterocycle substituents or "heterocyclic substituents" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is 2-, 3- or 4-pyridyl. Thienyl is 2- or 3-thienyl. Furyl is 2- or 3-furyl.

Also included are the corresponding N-oxides of these compounds, i.e., for example, 1-oxy-2-, -3- or -4-pyridyl.

Also included are mono- or polybenzofused derivatives of these heterocycles.

The heterocyclic rings or heterocyclic substituents may be mono- or polysubstituted by suitable groups, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2$NH($C_1$-$C_6$)-alkyl, $SO_2$N [($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N(($C_1$-$C_6$)-alkyl)($CH_2$)$_n$-aryl, $SO_2$—N(($C_1$-$C_6$)-alkyl)($CH_2$)$_n$-heterocycle, $SO_2$—N(($CH_2$)$_n$-aryl)$_2$, $SO_2$—N(($CH_2$)$_n$-heterocycle)$_2$ where n may be 0-6 and the aryl radical or heterocyclic radical may be up to disubstituted by F, Cl, Br, OH, $CF_3$, $NO_2$, CN, $OCF_3$, O—$(C_1$-$C_6)$-alkyl, $(C_1$-$C_6)$-alkyl or $NH_2$;
C(=NH)($NH_2$), $NH_2$, NH—$(C_1$-$C_6)$-alkyl, N(($C_1$-$C_6)$-alkyl)$_2$, NH($C_1$-$C_7$)-acyl, NH—COO—$(C_1$-$C_6)$-alkyl, NH—CO-aryl, NH—CO-heterocycle, NH—COO-aryl, NH—COO-heterocycle, NH—CO—NH—$(C_1$-$C_6)$-alkyl, NH—CO—NH-aryl, NH—CO—NH-heterocycle, N(($C_1$-$C_6)$-alkyl)-CO—$(C_1$-$C_6)$-alkyl, N(($C_1$-$C_6)$-alkyl)-COO—$(C_1$-$C_6)$-alkyl, N(($C_1$-$C_6)$-alkyl)-CO-aryl, N(($C_1$-$C_6)$-alkyl)-CO-heterocycle, N(($C_1$-$C_6)$-alkyl)-COO-aryl, N(($C_1$-$C_6)$-alkyl)-COO-heterocycle, N(($C_1$-$C_6)$-alkyl)-CO—NH—$(C_1$-$C_6)$-alkyl), N(($C_1$-$C_6)$-alkyl)-CO—NH-aryl, N(($C_1$-$C_6)$-alkyl)-CO—NH-heterocycle, N(($C_1$-$C_6)$-alkyl)-CO—N(($C_1$-$C_6)$-alkyl)$_2$, N(($C_1$-$C_6)$-alkyl)-CO—N(($C_1$-$C_6)$-alkyl)-aryl, N(($C_1$-$C_6)$-alkyl)-CO—N(($C_1$-$C_6)$-alkyl)-heterocycle, N(($C_1$-$C_6)$-alkyl)-CO—N-(aryl)$_2$, N(($C_1$-$C_6)$-alkyl)-CO—N-(heterocycle)$_2$, N(aryl)-CO—$(C_1$-$C_6)$-alkyl, N(heterocycle)-CO—$(C_1$-$C_6)$-alkyl, N(aryl)-COO—$(C_1$-$C_6)$-alkyl, N(heterocycle)-COO—$(C_1$-$C_6)$-alkyl, N(aryl)-CO-aryl, N(heterocycle)-CO-aryl, N(aryl)-COO-aryl, N(heterocycle)-COO-aryl, N(aryl)-CO—NH—$(C_1$-$C_6)$-alkyl), N(heterocycle)-CO—NH—$(C_1$-$C_6)$-alkyl), N(aryl)-CO—NH-aryl, N(heterocycle)-CO—NH-aryl, N(aryl)-CO—N(($C_1$-$C_6)$-alkyl)$_2$, N(heterocycle)-CO—N(($C_1$-$C_6)$-alkyl)$_2$, N(aryl)-CO—N(($C_1$-$C_6)$-alkyl)-aryl, N(heterocycle)-CO—N(($C_1$-$C_6)$-alkyl)-aryl, N(aryl)-CO—N-(aryl)$_2$, N(heterocycle)-CO—N-(aryl)$_2$, aryl, O—$(CH_2)_n$-aryl and O—$(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, O—$(C_1$-$C_6)$-alkyl, $(C_1$-$C_6)$-alkyl, $NH_2$, NH($C_1$-$C_6)$-alkyl, N(($C_1$-$C_6)$-alkyl)$_2$, $SO_2$—$CH_3$, COOH, COO—$(C_1$-$C_6)$-alkyl or $CONH_2$.

The compound(s) of the formula (I) may also be optionally combined and/or administered with additional active ingredients.

The amount of a compound of the formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg to 50 mg) per day per kilogram of bodyweight, for example 3-10 mg/kg/day. An intravenous dose may, for example, be in the range from 0.3 mg to 1.0 mg/kg and may suitably be administered as an infusion of from 10 ng to 100 ng per kilogram per minute. Suitable infusion solutions for these purposes may, for example, contain from 0.1 ng to 10 mg, typically from 1 ng to 10 mg, per milliliter. Single doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of the formula I may be used for therapy of the abovementioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The carrier may be a solid or a liquid or both and is preferably formulated with the compound as a single dose, for example as a tablet, which may contain from 0.05 to 95% by weight of the active ingredient. Further pharmaceutically active substances may likewise be present, including further compounds of the formula I. The inventive pharmaceutical compositions may be produced by one of the known pharmaceutical methods which consist essentially in mixing the constituents with pharmacologically acceptable carriers and/or excipients.

Inventive pharmaceutical compositions are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of the formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units, for example capsules, cachets, lozenges or tablets, each of which contains a certain amount of the compound of the formula I; as powder or granules; as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional constituents) are brought into contact. In general, the compositions are prepared by uniform and homogeneous mixing of the active ingredient with a liquid carrier and/or finely divided solid carrier, after which the product is shaped if necessary. For example, a tablet can thus be produced by compressing or shaping a powder or granules of the compound, optionally with one or more additional constituents. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain a compound of the formula I with a flavoring, customarily sucrose, and gum arabic or tragacanth, and pastilles which include the compound in an inert base, such as gelatin and glycerol or sucrose and gum arabic.

Suitable pharmaceutical compositions for parenteral administration preferably include sterile aqueous preparations of a compound of the formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. Injectable compositions according to the invention generally contain from 0.1 to 5% by weight of the active compound.

Suitable pharmaceutical compositions for rectal administration are preferably in the form of single dose suppositories. These can be prepared by mixing a compound of the formula I with one or more conventional solid carriers, for example cocoa buffer, and shaping the resulting mixture.

Suitable pharmaceutical compositions for topical application on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters suitably contain the active ingredient in an optionally buffered aqueous solution, dissolved and/or dispersed in an adhesive or dispersed in a polymer. A suitable active ingredient concentration is from approx. 1% to 35%, preferably from approx. 3% to 15%. A particular means of releasing the active ingredient may be by electrotransport or iontophoresis, as described, for example, in Pharmaceutical Research, 2(6): 318 (1986).

Further useful active ingredients for combination products are as follows:

All antidiabetics mentioned in the Rote Liste 2001, chapter 12. They can be combined with the inventive compounds of the formula I, in particular for synergistic enhancement of action. The active ingredient combination can be administered either by separately administering the active ingredients to the patient or in the form of combination products in which a plurality of active ingredients are present in one pharmaceutical preparation. Most of the active ingredients listed hereinbelow are disclosed in USP Dictionary of USAN and International Drug Names, US Pharmacopeia, Rockville 2001.

Antidiabetics include insulin and insulin derivatives, for example Lantus® (see www.lantus.com) or HMR 1964, fast-acting insulins (see U.S. Pat. No. 6,221,633 to Ertl et. al.), GLP-1 derivatives, for example those disclosed in WO 98/08871 of Novo Nordisk A/S, and orally active hypoglycemic active ingredients.

The orally active hypoglycemic active ingredients preferably include sulfonylureas, biguanidines, meglitinides, oxadiazolidinediones, thiazolidinediones, glucosidase inhibitors, glucagon antagonists, GLP-1 agonists, potassium channel openers, for example those disclosed in WO 97/26265 and WO 99/03861 of Novo Nordisk A/S, insulin sensitizers, inhibitors of liver enzymes which are involved in the stimulation of gluconeogenesis and/or glycogenolysis, modulators of glucose uptake, compounds which alter lipid metabolism such as anti-hyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin or rosuvastatin.

In one embodiment of the invention, the compounds of the formula I are administered in combination with a cholesterol absorption inhibitor, for example, ezetimibe, tiqueside, pamaqueside, or with a compound as described in PCT/EP 2004/00269, PCT/EP 2003/05815, PCT/EP 2003/05814, PCT/EP 2003/05816, EP 0114531 or U.S. Pat. No. 6,498,156.

In one embodiment of the invention, the compounds of the formula I are administered in combination with a PPAR gamma agonist, for example, rosiglitazone, pioglitazone, JTT-501 or GI 262570.

In one embodiment of the invention, the compounds of the formula I are administered in combination with PPAR alpha agonist, for example, GW 9578, GW 7647.

In one embodiment of the invention, the compounds of the formula I are administered in combination with a mixed PPAR alpha/gamma agonist, for example, GW 1536, AVE 8042, AVE 8134, AVE 0847, or as described in PCT/US 11833, PCT/US 11490, DE10142734.4.

In one embodiment of the invention, the compounds of the formula I are administered in combination with a fibrate, for example fenofibrate, clofibrate or bezafibrate.

In one embodiment of the invention, the compounds of the formula I are administered in combination with an MTP inhibitor, for example implitapide, BMS-201038 or R-103757.

In one embodiment of the invention, the compounds of the formula I are administered in combination with a bile acid absorption inhibitor (see, for example, U.S. Pat. Nos. 6,245,744 or 6,221,897), for example HMR 1741.

In one embodiment of the invention, the compounds of the formula I are administered in combination with a CETP inhibitor, for example JTT-705.

In one embodiment of the invention, the compounds of the formula I are administered in combination with a polymeric bile acid adsorber, for example cholestyramine, colesevelam.

In one embodiment of the invention, the compounds of the formula I are administered in combination with an LDL receptor inducer (see U.S. Pat. No. 6,342,512), for example HMR1171 or HMR1586.

In one embodiment of the invention, the compounds of the formula I are administered in combination with an ACAT inhibitor, for example avasimibe.

In one embodiment of the invention, the compounds of the formula I are administered in combination with an antioxidant, for example OPC-14117.

In one embodiment of the invention, the compounds of the formula I are administered in combination with a lipoprotein lipase inhibitor, for example NO-1886.

In one embodiment of the invention, the compounds of the formula I are administered in combination with an ATP citrate lyase inhibitor, for example SB-204990.

In one embodiment of the invention, the compounds of the formula I are administered in combination with a squalene synthetase inhibitor, for example BMS-188494.

In one embodiment of the invention, the compounds of the formula I are administered in combination with a lipoprotein (a) antagonist, for example CI-1027 or nicotinic acid.

In one embodiment of the invention, the compounds of the formula I are administered in combination with a lipase inhibitor, for example orlistat.

In one embodiment of the invention, the compounds of the formula I are administered in combination with insulin.

In one embodiment, the compounds of the formula I are administered in combination with a sulfonylurea, for example tolbutamide, glibenclamide, glipizide or glimepiride.

In one embodiment, the compounds of the formula I are administered in combination with a biguanide, for example metformin.

In yet another embodiment, the compounds of the formula I are administered in combination with a meglitinide, for example repaglinide.

In one embodiment, the compounds of the formula I are administered in combination with a thiazolidinedione, for example troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compounds of the formula I are administered in combination with an α-glucosidase inhibitor, for example miglitol or acarbose.

In one embodiment, the compounds of the formula I are administered in combination with adenosine A1 agonists, for example those which are described in EP 0912520 or PCT/EP06749.

In one embodiment, the compounds of the formula I are administered in combination with an active ingredient which acts on the ATP-dependent potassium channel of the beta cells, for example tolbutamide, glibenclamide, glipizide, glimepiride or repaglinide.

In one embodiment, the compounds of the formula I are administered in combination with more than one of the abovementioned compounds, for example in combination with a sulfonylurea and metformin, a sulfonylurea and acarbose, repaglinide and metformin, insulin and a sulfonylurea, insulin and mefformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)-methyl]cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxo-ethyl]amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), CB1 (cannabinoid receptor 1) receptor antagonists (e.g. rimonabant or the active ingredients specified in WO 02/28346), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethyl-carbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine or doprexin), lipase/amylase inhibitors (see, for example, WO 00/40569), PPAR modulators (see, for example, WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphatamine or amphetamine.

In one embodiment, the other active ingredient is fenfluramine or dexfenfluramine.

In one embodiment, the other active ingredient is sibutramine.

In one embodiment, the other active ingredient is orlistat.

In one embodiment, the other active ingredient is mazindol or phentermine.

In another embodiment, the other active ingredient is rimonabant.

In one embodiment, the compounds of the formula I are administered in combination with dietary fiber materials, preferably insoluble dietary fiber materials (see, for example, Carob/Caromax® (Zunft H J; et al., Carob pulp preparation for treatment of hypercholesterolemia, ADVANCES IN THERAPY (2001 September-October), 18(5), 230-6.) Caromax is a carob-containing product supplied by Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can also be administered in the form of foodstuffs, for example, in bakery products or muesli bars.

It will be appreciated that any suitable combination of the compounds according to the invention with one or more of the abovementioned compounds and optionally one or more further pharmacologically active substances is regarded as being covered by the scope of protection of the present invention.

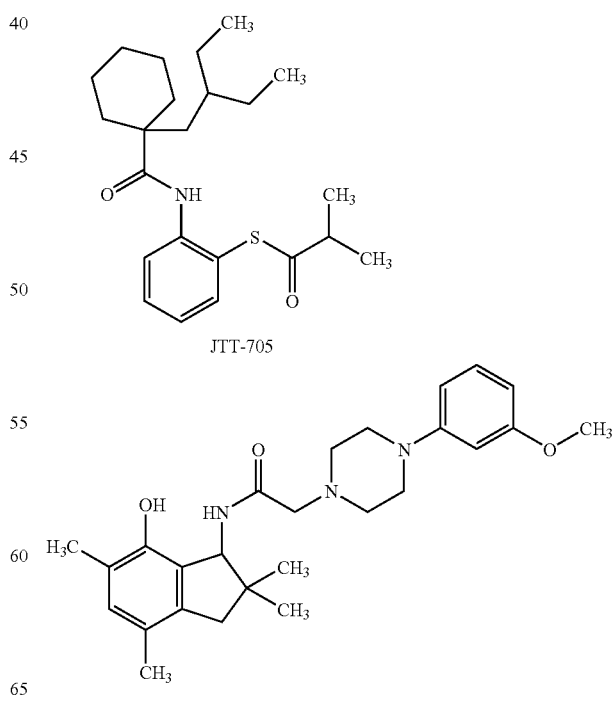

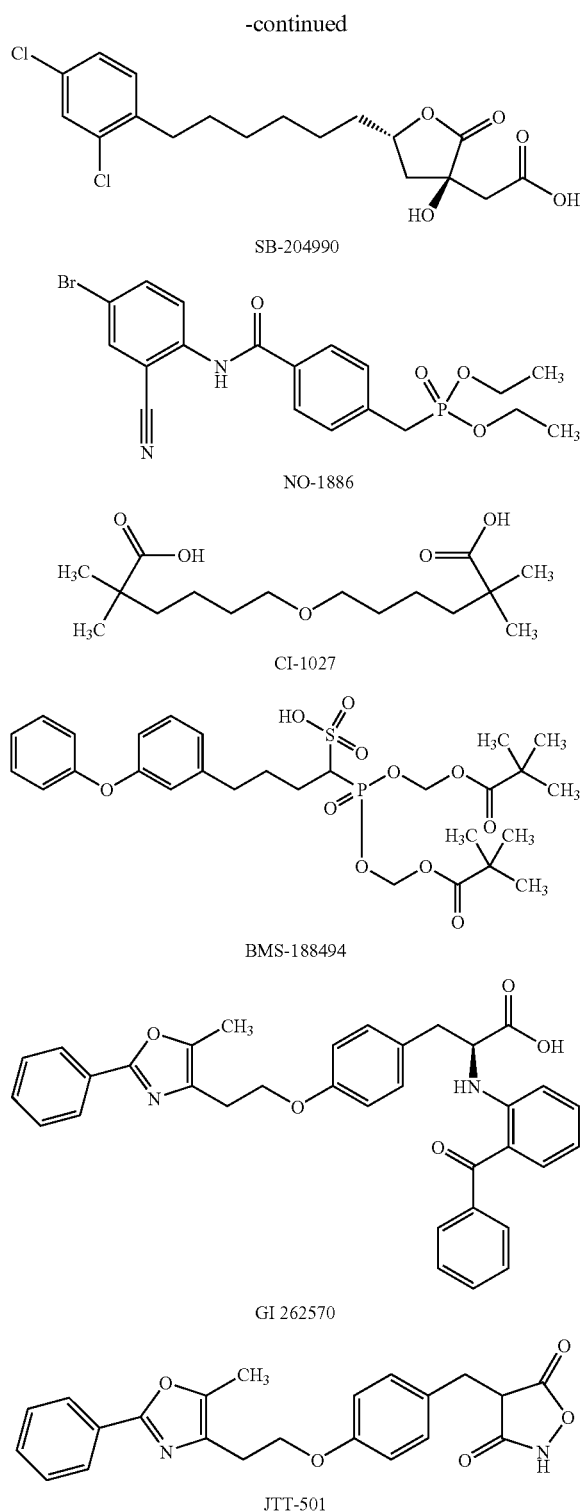

The compounds of the formula I can be prepared by reacting suitable starting materials of the formula II in which X is a leaving group, such as chlorine, bromine, iodine, sulfonyloxy, sulfinyl or sulfoxyl, with a compound of the formula IV optionally in the presence of suitable bases and in suitable solvents.

In the cases where R11 is hydrogen, it may be appropriate to use the radical IV in a form protected on the nitrogen function and to detach the protecting group again on completion of reaction with II. Such suitable protecting groups and the processes for their introduction and detachment are known (see: Theodora W. Greene and Peter G. M. Wuts, Protective Groups in Organic Synthesis, 3rd Edition, John Wiley & Sons, Inc., New York, 1999). The halogen compounds of the formula II can be obtained by known processes, for example by halogenating the corresponding H, hydroxyl or thio compound (formula II, X=H, OH or SH). Suitable halogenating agents may, by way of example, be halogens such as chlorine and bromine, N-bromosuccinimide, phosphorus pentachloride or phosphorus oxychloride.

The synthesis of compounds of the formula II is described in the literature. They may be prepared, for example, by condensing substituted diaminobenzene derivatives with aldehydes in the presence of an oxidizing agent (for example atmospheric oxygen, oxygen, iodine, oxone, quinones, peroxides, etc.), or alternatively with carboxylic acids, nitriles or amides, without or in the presence of a catalyst.

The bicyclic amines IV can be synthesized by processes known from the literature.

For instance, the preparation of various derivatives of this structure class, for example of octahydropyrrolo(3,4-b) pyrrole and 1-methyloctahydropyrrolo[3,4-b]pyrrole, has been described in EP 0 393 424.

Some derivatives of the formula IV, for example octahydropyrrolo[3,4-b]pyridine or octahydropyrrolo[3,4-c]pyridine, are commercially available.

The tabulated examples listed below serve to illustrate the invention but without restricting it. The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow.

TABLE 1

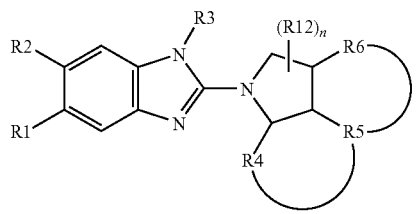

| Ex. | R1 | R2 | R3 | R4—R5 | R5—R6 | R12 | Salt |
|---|---|---|---|---|---|---|---|
| 1 | H | Benzoylamino | $CH_2$—$CH$=$C(CH_3)_2$ | —$CH_2$—$NH$—$CH_2$— | R6 = H | H | TFA |
| 2 | H | Benzoylamino | $CH_2$—$CH$=$C(CH_3)_2$ | R4 = H | —$CH_2$—$NH$—$CH_2$— | H | TFA |
| 3 | H | Benzylamino-carbonyl | Benzyl | —$CH_2$—$NH$—$CH_2$— | R6 = H | H | TFA |
| 4 | Benzylamino-carbonyl | H | Benzyl | —$CH_2$—$NH$—$CH_2$— | R6 = H | H | TFA |
| 5 | H | Benzylamino-carbonyl | Benzyl | R4 = H | —$CH_2$—$NH$—$CH_2$— | H | TFA |
| 6 | Benzylamino-carbonyl | | Benzyl | R4 = H | —$CH_2$—$NH$—$CH_2$— | H | TFA |

The compounds of the formula I feature favorable effects on lipid and carbohydrate metabolism; in particular, they lower the blood sugar level and are suitable for the treatment of type II diabetes, of insulin resistance, of dislipidemias and of metabolic syndrome/syndrome X. Moreover, the compounds are suitable for the treatment and prophylaxis of arteriosclerotic manifestations. The compounds can be used alone or in combination with further blood sugar-lowering active ingredients. The compounds act as DPP IV (dipeptidyl peptidase IV) inhibitors and are also suitable for the treatment of disorders of perception and other psychiatric indications, for example depressions, anxiety states, anxiety neuroses, schizophrenia, and for the treatment of disorders associated with the circadian rhythm, for weight reduction in mammals, for the treatment of immune disorders and for the treatment of drug abuse.

They are additionally suitable for the treatment of cancer, arthritis, osteoarthritis, osteoporosis, sleep disorders, sleep apnea, masculine and feminine sexual disorders, inflammations, acne, pigmentation of the skin, disorders of steroid metabolism, skin diseases, psoriasis, mycoses, neurodegenerative disorders, multiple sclerosis and Alzheimer's disease.

The efficacy of the compounds was tested as follows:

Measurement of the DPP-IV Activity:

Material:
 DPP-IV from porcine kidneys (Sigma, Munich)
 H-Ala-Pro-AFC (Bachem, Weil am Rhein)

Test Conditions:
 DPP-IV (1 mU/ml, end concentration)
 H-Ala-Pro-AFC (15 μm end concentration) in Tris/HCl (40 mM, pH 7.4), total volume 0.2 ml The reaction was performed at room temperature for different periods (typically 10 minutes) and stopped at the end of the reaction by adding 20 μl of $ZnCl_2$ (1 M). The conversion of H-Ala-Pro-AFC was determined fluorimetrically by measuring the emission at 535 nm on excitation at 405 nm. In the case of addition of inhibitors, the buffer volume added was adjusted such that a total volume of the test mixture of 200 μl was maintained.

% inhibition at a fixed concentration was calculated as follows:

$$(1-\text{enzyme activity}_{inhibited\ reaction}/\text{enzyme activity}_{uninhibited\ reaction}) \times 100$$

TABLE 2

Biological activity of working examples:

| Example | % inhibition at 30 μm |
|---|---|
| 1 | 25 |

TABLE 3

Biological activity of working examples:

| Example | % inhibition at 10 μm |
|---|---|
| 5 | 87 |
| 6 | 96 |

It can seen from the tables that the compounds of the formula I inhibit the activity of the DPP-IV (dipeptidyl peptidase IV) and are thus suitable for lowering the blood sugar level.

The preparation of the working examples will be described in detail hereinafter:

EXAMPLE 1

N-[2-(Hexahydropyrrolo[3,4-b]pyrrol-2-yl)-1-(3-methylbut-2-enyl)-1H-benzimidazol-6-yl]-benzamide a) 2-Bromo-6-nitro-1H-benzimidazole

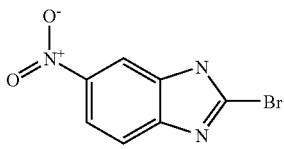

A suspension of 5.0 g (25.61 mmol) of 6-nitro-1H-benzimidazole-2-thiol in 30 ml of methanol and 10 ml of hydrogen bromide (48% in water) was cooled to 5-10° C. and admixed with 5.7 ml (111 mmol) of bromine. Subsequently, the mixture was stirred at 5-10° C. for 1.5 hours and poured onto ice-water. The red precipitate was filtered off with suction, washed with water and dried at 40° C. under reduced pressure. 4.82 g (78%) of the desired product were obtained.

b) 2-Bromo-1-(3-methylbut-2-enyl)-5/6-nitro-1H-benzimidazole

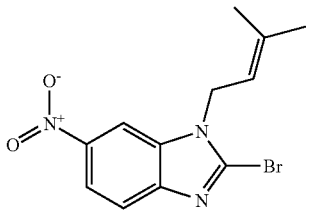

1.0 g (4.13 mmol) of 2-bromo-5/6-nitro-1H-benzimidazole was dissolved in 20 ml of dimethylformamide, admixed with 2.02 g (6.20 mmol) of cesium carbonate and stirred at room temperature for 30 minutes. 0.677 g (4.54 mmol) of 1-bromo-3-methyl-2-butene was added and the reaction mixture was stirred at room temperature for 18 hours. The precipitate was filtered off with suction and washed with dimethylformamide. The filtrate was concentrated under reduced pressure and the residue was partitioned between dichloromethane and water. The organic phase was dried and concentrated under reduced pressure. The crude mixture was separated on silica gel (eluent: heptane/ethyl acetate, gradient: 90/10 to 0/100). 766 mg (60%) of the desired product were obtained.

MS: m/z=311 (M+H)$^+$.

c) tert-Butyl 1-[1-(3-methylbut-2-enyl)-6-nitro-1H-benzimidazol-2-yl]hexahydropyrrolo-[3,4-b]pyrrole-5-carboxylate

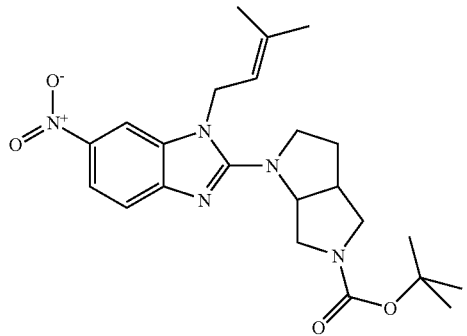

81 mg (0.38 mmol) of tert-butyl hexahydropyrrolo[3,4-b]pyrrole-5-carboxylate were dissolved in 1 ml of dimethylformamide and admixed with 170 mg (0.52 mmol) of cesium carbonate, and stirred at room temperature for 30 minutes. 108 mg (0.35 mmol) of 2-bromo-1-(3-methylbut-2-enyl)-5/6-nitro-1H-benzimidazole were dissolved in 5 ml of dimethylformamide and added slowly. The reaction mixture was stirred at 90° C. for 9 hours and then partitioned between dichloromethane and water. The organic phase was dried and concentrated under reduced pressure. The crude mixture was separated on silica gel (eluent: heptane/ethyl acetate, gradient: 90/10 to 0/100). 44 mg (29%) of tert-butyl 1-[1-(3-methylbut-2-enyl)-5-nitro-1H-benzimidazol-2-yl]hexahydropyrrolo[3,4-b]pyrrole-5-carboxylate and 49 mg (32%) and 49 mg (32%) of the desired product were obtained.

MS: m/z=442 (M+H)$^+$.

d) tert-Butyl 1-[6-amino-1-(3-methylbut-2-enyl)-1H-benzimidazol-2-yl]hexahydropyrrolo-[3,4-b]pyrrole-5-carboxylate

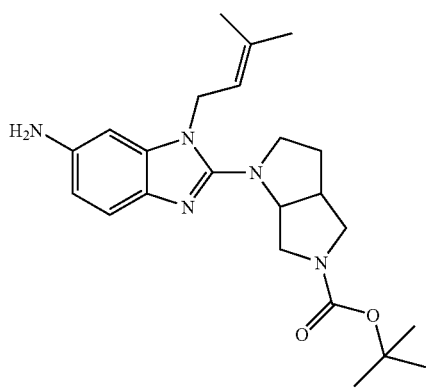

A solution of 49 mg (0.11 mmol) of tert-butyl 1-[1-(3-methylbut-2-enyl)-6-nitro-1H-benzimidazol-2-yl]hexahydropyrrolo[3,4-b]pyrrole-5-carboxylate in 7.5 ml of ethanol was added dropwise to a suspension of 62 mg (1.11 mmol) of iron and 11 mg (0.20 mmol) of ammonium chloride in 0.75 ml of water, and the mixture was boiled at reflux for 3 hours. The catalyst was filtered off and washed with ethanol. The filtrate was concentrated under reduced pressure. The 43 mg of the desired product thus obtained were used in the next stage without further purification.

e) tert-Butyl 1-[6-benzoylamino-1-(3-methylbut-2-enyl)-1H-benzimidazol-2-yl]hexahydropyrrolo[3,4-b]pyrrole-5-carboxylate

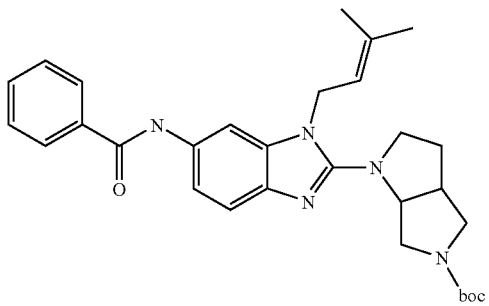

17 mg (0.05 mmol) of cesium carbonate were added to a solution of 43 mg (0.1 mmol) of tert butyl 1-[6-amino-1-(3-methylbut-2-enyl)-1H-benzimidazol-2-yl]hexahydropyrrolo-[3,4-b]pyrrole-5-carboxylate in 5 ml of dimethylformamide, and the mixture was stirred at room temperature for 30 minutes. Subsequently, 12 μl (0.10 mmol) of benzoyl chloride were added and the mixture was stirred at room temperature for 20 hours. The reaction mixture was concentrated under reduced pressure and purified by means of preparative HPLC (acetonitrile/water+0.5% trifluoroacetic acid, gradient: 20/80 to 100/0). 10 mg (20%) of the desired compound were obtained.

f) N-[2-(Hexahydropyrrolo[3,4-b]pyrrol-2-yl)-1-(3-methylbut-2-enyl)-3H-benzimidazol-6-yl]benzamide

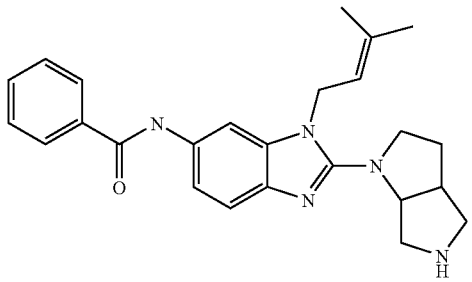

10 mg (0.02 mmol) of tert-butyl 1-[6-benzoylamino-1-(3-methylbut-2-enyl)-1H-benzimidazol-2-yl]-hexahydropyrrolo[3,4-b]pyrrole-5-carboxylate were dissolved in 200 μl of trifluoroacetic acid and 200 μl of water, and stirred at room temperature for 19 hours. The reaction mixture was diluted with water and freeze-dried. 10 mg (95%) of the desired product were obtained.

MS: m/z=416 (M+H)$^+$.

EXAMPLE 2

N-[2-(Hexahydropyrrolo[3,4-c]pyrrol-1-yl)-1-(3-methylbut-2-enyl)-1H-benzimidazol-6-yl]benzamide (A003454047A)

a) tert-Butyl 5-[1-(3-methylbut-2-enyl)-6-nitro-1H-benzimidazol-2-yl]hexahydropyrrolo[3,4-c]pyrrole-2-carboxylate

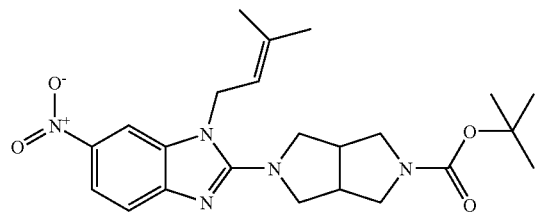

111 mg (0.52 mmol) of tert-butyl hexahydropyrrolo[3,4-c]pyrrole-2-carboxylate were dissolved in 1 ml of dimethylformamide and admixed with 170 mg (0.52 mmol) of cesium carbonte, and stirred at room temperature for 30 minutes. 108 mg (0.35 mmol) of 2-bromo-1-(3-methylbut-2-enyl)-5/6-nitro-1H-benzimidazole (example 1b) were dissolved in 5 ml of dimethylformamide and added slowly. The reaction mixture was stirred in a microwave at 150° C. for 1.5 hours and then concentrated under reduced pressure. The crude mixture was partitioned between dichloromethane and water. The organic phase was dried and concentrated under reduced pressure. The crude mixture was separated on silica gel (eluent: heptane/ethyl acetate, gradient: 90/10 to 0/100). 74 mg of a mixed fraction of the desired product with tert-butyl 5-[1-(3-methylbut-2-enyl)-5-nitro-1H-benzimidazol-2-yl]hexahydropyrrolo[3,4-c]pyrrole-2-carboxylate and 44 mg (29%) of the desired product were obtained.

MS: m/z=442 (M+H)$^+$.

b) tert-Butyl 5-[6-amino-1-(3-methylbut-2-enyl)-1H-benzimidazol-2-yl]hexahydropyrrolo-[3,4-c]pyrrole-2-carboxylate

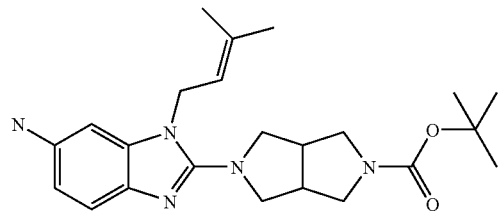

A solution of 44 mg (0.10 mmol of tert-butyl 5-[1-(3-methylbut-2-enyl)-6-nitro-1H-benzimidazol-2-yl]hexahydropyrrolo[3,4-c]pyrrole-2-carboxylate in 7.5 ml of ethanol was added dropwise to a suspension of 56 mg (1.00 mmol) of iron and 10 mg (0.18 mmol) of ammonium chloride in 0.75 ml of water, and the mixture was boiled at reflux for 3 hours. The catalyst was filtered off and washed with ethanol. The filtrate was concentrated under reduced pressure. The 35 mg of the desired product thus obtained were used in the next stage without further purification.

c) tert-Butyl 5-[6-benzoylamino-1-(3-methylbut-2-enyl)-1H-benzimidazol-2-yl]hexahydropyrrolo[3,4-c]pyrrole-2-carboxylate

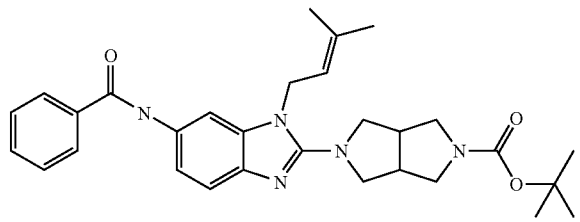

14 mg (0.04 mmol) of cesium carbonate were added to a solution of 35 mg (0.09 mmol) of tert-butyl 5-[6-amino-1-(3-methylbut-2-enyl)-1H-benzimidazol-2-yl]hexahydropyrrolo[3,4-c]pyrrole-2-carboxylate in 5 ml of dimethylformamide, and the mixture was stirred at room temperature for 30 minutes. Subsequently, 10 µl (0.08 mmol) of benzoyl chloride were added and the mixture was stirred at room temperature for 20 hours. The reaction mixture was concentrated under reduced pressure and purified by means of preparative HPLC (acetonitrile/water+0.5% trifluoroacetic acid, gradient: 20/80 to 100/0). 10 mg (22% of the desired compound were obtained.

d) N-[2-(Hexahydropyrrolo[3,4-c]pyrrol-1-yl)-1-(3-methylbut-2-enyl)-1H-benzimidazol-6-yl]-benzamide

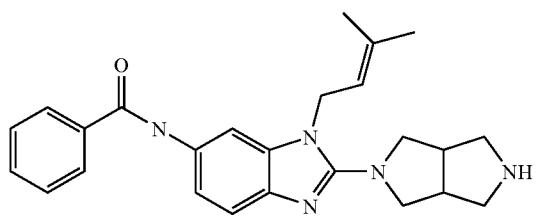

10 mg (0.02 mmol) of tert-butyl 5-[6-benzoylamino-1-(3-methylbut-2-enyl)-1H-benzimidazol-2-yl]hexahydropyrrolo[3,4-c]pyrrole-2-carboxylate were dissolved in 200 µl of trifluoroacetic acid and 200 µl of water, and stirred at room temperature for 19 hours. The reaction mixture was diluted with water and freeze-dried. 10 mg (95%) of the desired product were obtained.

MS: m/z=416 (M+H)$^+$.

What is claimed is:

1. A compound of formula I

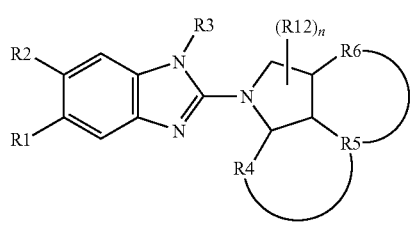

I wherein:
R1 and R2 are each independently selected from the group consisting of H, CON(R20)R21, N(R22)COR23 or N(R24)R25, wherein the two R1 and R2 substituents cannot both be hydrogen simultaneously;
R20 and R21 are each independently selected from the group consisting of H, $(C_1\text{-}C_{10})$-alkyl, $(C_3\text{-}C_{10})$-cycloalkyl, $(C_2\text{-}C_{10})$-alkenyl, $(C_2\text{-}C_{10})$-alkynyl, $(C_6\text{-}C_{10})$-aryl, heterocycle, $(C_1\text{-}C_6)$-alkylene-$(C_6\text{-}C_{10})$-aryl and $(C_1\text{-}C_6)$-alkylene-$(C_6\text{-}C_{10})$-heterocycle, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1\text{-}C_6)$-alkyl, O—$(C_1\text{-}C_6)$-alkyl, S—$(C_1\text{-}C_6)$-alkyl, S(O)—$(C_1\text{-}C_6)$-alkyl or $S(O)_2$—$(C_1\text{-}C_6)$-alkyl; with the exception that R20 and R21 cannot be phenyl groups fused to nitrogen-containing 5-membered hetero-aromatic rings
R22 and R23 are selected from the group consisting of H, $(C_1\text{-}C_{10})$-alkyl, $(C_3\text{-}C_{10})$-cycloalkyl, $(C_2\text{-}C_{10})$-alkenyl, $(C_2\text{-}C_{10})$-alkynyl, $(C_6\text{-}C_{10})$-aryl, heterocycle, $(C_1\text{-}C_6)$-alkylene-$(C_6\text{-}C_{10})$-aryl, $(C_1\text{-}C_6)$-alkylene-$(C_6\text{-}C_{10})$-heterocycle and $S(O)_2$-aryl, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1\text{-}C_6)$-alkyl, O—$(C_1\text{-}C_6)$-alkyl, S—$(C_1\text{-}C_6)$-alkyl, S(O)—$(C_1\text{-}C_6)$-alkyl or $S(O)_2$—$(C_1\text{-}C_6)$-alkyl;
R24 and R25 are each independently selected from the group consisting of H, $(C_1\text{-}C_{10})$-alkyl, $(C_3\text{-}C_{10})$-cycloalkyl, $(C_2\text{-}C_{10})$-alkenyl, $(C_2\text{-}C_{10})$-alkynyl, $(C_6\text{-}C_{10})$-aryl, heterocycle, $(C_1\text{-}C_6)$-alkylene-$(C_6\text{-}C_{10})$-aryl, $(C_1\text{-}C_6)$-alkylene-$(C_6\text{-}C_{10})$-heterocycle and $S(O)_2$-aryl, where the alkyl, cycloalkyl, alkenyl, alkynyl, alkylene, aryl and heterocycle substituents may be mono- or polysubstituted by F, Cl, Br, I, CN, $NO_2$, SH, OH, $(C_1\text{-}C_6)$-alkyl, O—$(C_1\text{-}C_6)$-alkyl, S—$(C_1\text{-}C_6)$-alkyl, S(O)—$(C_1\text{-}C_6)$-alkyl or $S(O)_2$—$(C_1\text{-}C_6)$-alkyl;
R3 is independently selected from the group consisting of H, $(C_1\text{-}C_{10})$-alkyl, $(C_3\text{-}C_{10})$-cycloalkyl, $(C_2\text{-}C_{10})$-alkenyl, $(C_2\text{-}C_{10})$-alkynyl, $(C_6\text{-}C_{10})$-aryl and heterocycle, where the alkyl, cycloalkyl, alkenyl, alkynyl, aryl and heterocycle substituents may be mono- or polysubstituted by F, Cl, Br, I, CN, $NO_2$, SH, OH, $(C_1\text{-}C_6)$-alkyl, —$CF_3$, —$OCF_3$, —$SCF_3$, $(C_2\text{-}C_6)$-alkenyl, $(C_2\text{-}C_6)$-alkynyl, OR7, $OP(O)(OR7)_2$, N(R7)R8, N(R7)CON(R7)R8, COR7, OCOR7, OCOO(R7), COOR7, CON(R7)R8, OCON(R7)R8, $(C_1\text{-}C_6)$-alkylene-OR7, $(C_1\text{-}C_6)$-alkylene-N(R7)R8, $(C_1\text{-}C_6)$-alkylene-N(R7)$S(O)_2$R7, $(C_1\text{-}C_6)$-alkylene-SR7, $(C_1\text{-}C_6)$-alkylene-S(O)R7, $(C_1\text{-}C_6)$-alkylene-$S(O)_2$R7, $(C_1\text{-}C_6)$-alkylene-$S(O)_2$NR7R8, $(C_1\text{-}C_6)$-alkylene-COR7, $(C_1\text{-}C_6)$-alkylene-COOR7, $(C_1\text{-}C_6)$-alkylene-CONR7R8, SR7, S(O)R7, $S(O)_2$R7, $S(O)_2$NR7R8, NR7$S(O)_2$R7, $(C_1\text{-}C_6)$-alkylene-$(C_3\text{-}C_{10})$-cycloalkyl, $(C_1\text{-}C_6)$-alkylene-$(C_6\text{-}C_{10})$-aryl, $(C_1\text{-}C_6)$-alkylene-heterocycle, $(C_3\text{-}C_{10})$-cycloalkyl, $(C_6\text{-}C_{10})$-aryl or heterocycle; with the exception that R3 cannot be an un-substituted or substituted piperidin-4-yl
R7, R8 are each independently selected from the group consisting of H, $(C_1\text{-}C_6)$-alkyl, —$CF_3$, $(C_3\text{-}C_{10})$-cycloalkyl, $(C_6\text{-}C_{10})$-aryl, heterocycle, $(C_1\text{-}C_6)$-alkylene-CONR9R10, CONR9R10, $(C_1\text{-}C_6)$-alkylene-COOR9, COOR9, COR9, $(C_1\text{-}C_6)$-alkylene-COR9, $(C_1\text{-}C_6)$-alkylene-OR9, $(C_1\text{-}C_6)$-alkylene-NR9R10, $(C_1\text{-}C_6)$-alkylene-SR9, $(C_1\text{-}C_6)$-alkylene-S(O)R9, $(C_1\text{-}C_6)$-alkylene-$S(O)_2$R9, S(O)R9, $S(O)_2$R9, $(C_1\text{-}C_4)$-alkylene-$(C_6\text{-}C_{10})$-aryl and $(C_1\text{-}C_4)$-alkylene-heterocycle;

R9, R10 are each independently selected from the group consisting of H, $(C_1-C_6)$-alkyl, $(C_1-C_6)$-alkylene-$(C_6-C_{10})$-aryl, —$(C_6-C_{10})$-aryl, heterocycle and $(C_1-C_6)$-alkylene-heterocycle;

R4 and R5 together form a 3-5-membered alkylene chain in which one $CH_2$ group has been replaced by NR11 where R6 is H or R12, or R5 and R6 together form a 3- to 5-membered alkylene chain in which one $CH_2$ group has been replaced by NR11 where R4 is H or R12; where the 3- to 5-membered alkylene chain may in each case may be mono- or polysubstituted by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ or O—$(C_1-C_6)$-alkyl, where the alkyl groups may be mono- or polysubstituted by F, Cl, Br or I;

R11 is selected from the group consisting of H, $(C_1-C_6)$-alkyl, $(C_3-C_8)$-cycloalkyl, $(C_1-C_4)$-alkylene-aryl and $(C_1-C_4)$-alkylene-heterocycle;

R12 is selected from the group consisting of F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ and O—$(C_1-C_6)$-alkyl, where the alkyl groups may be mono- or polysubstituted by F, Cl, Br or I; and n is 0, 1 or 2;

excluding compounds in which the substituents are simultaneously defined as follows:

R1 or R2 is CONR20R21 and R3 is hydrogen or $CH_3$;

or a physiologically compatible salt thereof.

2. The compound of the formula I as recited in claim 1, wherein

R1 and R2 are each independently selected from the group consisting of H, CON(R20)R21, N(R22)COR23 and NR24R25, where the two R1 and R2 substituents cannot both be hydrogen simultaneously;

R20 and R21 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl and $(C_1-C_6)$-alkylene-$(C_6-C_{10})$-heterocycle, wherein the alkyl, cycloalkyl, alkenyl, alkynyl, alkylene, aryl and heterocycle substituents may each be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or S(O)$_2$—$(C_1-C_6)$-alkyl;

with the exception that R20 and R21 cannot be phenyl groups fused to nitrogen-containing 5-membered hetero-aromatic rings;

R22 and R23 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle and S(O)$_2$-aryl, where the alkyl, cycloalkyl, alkenyl, alkynyl, alkylene, aryl and heterocycle substituents may each be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or S(O)$_2$—$(C_1-C_6)$-alkyl;

R24 and R25 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle and S(O)$_2$-aryl, where the alkyl, cycloalkyl, alkenyl, alkynyl, alkylene, aryl and heterocycle substituents may be mono- or polysubstituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or S(O)$_2$—$(C_1-C_6)$-alkyl;

R3 is selected from the group consisting of $(C_2-C_{10})$-alkyl, $(C_3-C_{10})$-cycloalkyl, $(C_2-C_{10})$-alkenyl, $(C_2-C_{10})$-alkynyl, $(C_6-C_{10})$-aryl and heterocycle, where the alkyl, cycloalkyl, alkenyl, alkynyl, aryl and heterocycle substituents may be mono- or polysubstituted by F, Cl, Br, I, CN, $NO_2$, SH, OH, $(C_1-C_6)$-alkyl, —$CF_3$, —$OCF_3$, —$SCF_3$, $(C_2-C_6)$-alkenyl, $(C_2-C_6)$-alkynyl, OR7, OP(O)(OR7)$_2$, N(R7)R8, N(R7)CON(R7)R8, COR7, OC(O)R7, OCO(O)R7, CO(O)R7, CON(R7)R8, OCON(R7)R8, $(C_1-C_6)$-alkylene-OR7, $(C_1-C_6)$-alkylene-N(R7)R8, $(C_1-C_6)$-alkylene-N(R7)S(O)$_2$R7, $(C_1-C_6)$-alkylene-SR7, $(C_1-C_6)$-alkylene-S(O)R7, $(C_1-C_6)$-alkylene-S(O)$_2$R7, $(C_1-C_6)$-alkylene-S(O)$_2$N(R7)R8, $(C_1-C_6)$-alkylene-COR7, $(C_1-C_6)$-alkylene-COOR7, $(C_1-C_6)$-alkylene-CONR7R8, SR7, S(O)R7, S(O)$_2$R7, S(O)$_2$NR7R8, NR7S(O)$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and heterocycle; with the exception that R3 cannot be an un-substituted or substituted piperidin-4-yl R7 and R8 are each independently selected from the group consisting of H, $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, S(O)R9, S(O)$_2$R9, $(C_1-C_4)$-alkylene-$(C_6-C_{10})$-aryl and $(C_1-C_4)$-alkylene-heterocycle;

R9 and R10 are each independently selected from the group consisting of H, $(C_1-C_6)$-alkyl, $(C_1-C_6)$-alkylene-$(C_6-C_{10})$-aryl, —$(C_6-C_{10})$-aryl, heterocycle and $(C_1-C_6)$-alkylene-heterocycle;

R4 and R5 together form a 3-5-membered alkylene chain in which one $CH_2$ group has been replaced by NR11 when R6 is H or R12, or R5 and R6 together form a 3- to 5-membered alkylene chain in which one $CH_2$ group has been replaced by NR11 when R4 is H or R12; where the 3- to 5-membered alkylene chain may in each case may be mono- or polysubstituted by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ or O—$(C_1-C_6)$-alkyl, where the alkyl groups may be mono- or polysubstituted by F, Cl, Br or I;

R11 is selected from the group consisting of H, $(C_1-C_6)$-alkyl, $(C_3-C_8)$-cycloalkyl, $(C_1-C_4)$-alkylene-aryl and $(C_1-C_4)$-alkylene-heterocycle;

R12 is selected from the group consisting of F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ and O—$(C_1-C_6)$-alkyl, where the alkyl groups may be mono- or polysubstituted by F, Cl, Br or I; and n is 0, 1 or 2;

or a pharmaceutically acceptable salt thereof.

3. A pharmaceutical composition comprising the compound of formula I as recited in claim 1 combined with one or more additional solvents, bulking agents, binders, lubricants, inert diluents and/or one (or more) surfactants/dispersants, excipients, thickening agents, buffers, polymers, stabilizers, binders, flavorants, and sweeteners for administration as a tablet, capsule, intravenous solution, transdermal gel, powder, oral solution, syrup, intranasal spray, or lozenge to a patient in need thereof.

4. A pharmaceutical composition comprising the compound of formula I as recited in claim 2 combined with one or more additional solvents, bulking agents, binders, lubricant, inert diluent and/or one (or more) surfactants/dispersants, excipients, thickening agents, buffers, polymers, stabilizers, binders, flavorants, sweeteners formulated as a pharmaceutical composition for administration as a tablet, capsule, intravenous solution, transdermal gel, powder, oral solution, syrup, intranasal spray, or lozenge to a patient in need thereof.

5. The pharmaceutical composition as recited in claim 3 further comprising at least one additional active ingredient.

6. The pharmaceutical composition as recited in claim 4 further comprising at least one additional active ingredient.

7. The pharmaceutical composition as recited in claim 5 further comprising one or more anti-diabetics, active hypoglycemic ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin agonists, H3 agonists, TNF agonists, CRF agonists, CRIB antagonists, urocortin agonists, β3 agonists, CB1 receptor antagonists, MSH (melanocyte-stimulating hormone) agonists, CCK agonists, serotonin reuptake inhibitors, mixed serotonin and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptin, doprexin), lipase/amylase inhibitors, PPAR modulators, RXR modulators or TR-β agonists or amphetamines.

8. The pharmaceutical composition as recited in claim 6 further comprising one or more anti-diabetics, active hypoglycemic ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin agonists, H3 agonists, TNF agonists, CRF agonists, CRIB antagonists, urocortin agonists, β3 agonists, CB1 receptor antagonists, MSH (melanocyte-stimulating hormone) agonists, CCK agonists, serotonin reuptake inhibitors, mixed serotonin and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptin, doprexin), lipase/amylase inhibitors, PPAR modulators, RXR modulators or TR-β agonists or amphetamines.

9. A method for the therapeutic reduction of a patients' blood sugar comprising the administration of the pharmaceutical composition of claim 3 to a patient in need thereof.

10. A method for the therapeutic reduction of a patients' blood sugar comprising the administration of the pharmaceutical composition of claim 4 to a patient in need thereof.

11. A method for the therapeutic reduction of a patients' blood sugar comprising the administration of the pharmaceutical composition of claim 7 to a patient in need thereof.

12. A method for the therapeutic reduction of a patients' blood sugar comprising the administration of the pharmaceutical composition of claim 8 to a patient in need thereof.

13. A method for the therapeutic treatment of type II diabetes comprising the administration of the pharmaceutical composition of claim 3 to a patient in need thereof.

14. A method for the therapeutic treatment of type II diabetes comprising the administration of the pharmaceutical composition of claim 4 to a patient in need thereof.

15. A method for the therapeutic treatment of type II diabetes comprising the administration of the pharmaceutical composition of claim 7 to a patient in need thereof.

16. A method for the therapeutic treatment of type II diabetes comprising the administration of the pharmaceutical composition of claim 8 to a patient in need thereof.

* * * * *

UNITED STATES PATENT AND TRADEMARK OFFICE
CERTIFICATE OF CORRECTION

PATENT NO. : 7,569,700 B2  Page 1 of 1
APPLICATION NO. : 11/855224
DATED : August 4, 2009
INVENTOR(S) : Elisabeth Defossa et al.

It is certified that error appears in the above-identified patent and that said Letters Patent is hereby corrected as shown below:

In column 16, line 67, delete "buffer," and insert -- butter, --, therefor.

In column 17, line 43, delete "biguanidines," and insert -- biguanides, --, therefor.

In column 19, line 23, delete "mefformin," and insert -- metformin, --, therefor.

In column 22, line 37, delete "X==H," and insert -- X = H, --, therefor.

In column 24, line 62, after "can" insert -- be --.

Signed and Sealed this

Third Day of August, 2010

David J. Kappos
*Director of the United States Patent and Trademark Office*